United States Patent [19]

Hategan

[11] 3,989,387

[45] Nov. 2, 1976

[54] METHOD AND APPARATUS FOR DETECTING OPTICAL DEFECTS IN TRANSPARENT SHEETS

[75] Inventor: Stephane Hategan, Charenton, France

[73] Assignee: Saint-Gobain Industries, Neuilly-sur-Seine, France

[22] Filed: Dec. 11, 1974

[21] Appl. No.: 531,610

Related U.S. Application Data

[63] Continuation-in-part of Ser. No. 290,528, Sept. 20, 1972, abandoned.

[30] Foreign Application Priority Data

Sept. 24, 1971 France .............................. 71.34556

[52] U.S. Cl. .............................. 356/239; 250/562; 250/572; 356/200
[51] Int. Cl.[2] ......................................... G01N 21/00
[58] Field of Search ........... 356/120, 199, 200, 201, 356/209, 237, 239; 250/572, 562, 563

[56] References Cited
UNITED STATES PATENTS

| | | | |
|---|---|---|---|
| 3,199,401 | 8/1965 | Sleighter et al. | 356/200 |
| 3,338,130 | 8/1967 | Gaffard | 250/572 X |
| 3,639,112 | 2/1972 | Poola | 356/120 X |
| 3,667,846 | 6/1972 | Nater et al. | 356/120 |

Primary Examiner—John K. Corbin
Assistant Examiner—Matthew W. Koren
Attorney, Agent, or Firm—Pennie & Edmonds

[57] ABSTRACT

Apparatus for detecting and measuring imperfections such as wedge, combing and lack of planarity in transparent sheets such as glass comprises an extended luminous source, focusing means to form a convergent beam containing an image of the source, a differential photoelectric cell positioned to receive that image after passage of that beam through, or reflection thereof at, the sheet, and circuit means connected with the cell for producing a changed output upon shift of the image on the cell due to changed refraction or reflection of the beam at the sheet produced by a defect. The beam of focused light is limited or stopped so that a cross-sectional dimension thereof is of the same order of magnitude as the width of typical defects in the sheets. According to the method of the invention the sheet is advanced in its own plane relatively to the source, focusing means, cell and stop, in a direction parallel to the width dimension of the defects in the sheet, this direction of motion being parallel to the said cross-sectional dimension of the beam.

13 Claims, 11 Drawing Figures

METHOD AND APPARATUS FOR DETECTING OPTICAL DEFECTS IN TRANSPARENT SHEETS

This application is a continuation-in-part of my application Ser. No. 290,528, filed Sept. 20, 1972, now abandoned.

The present invention has for its chief purpose the provision of apparatus and method for detecting and measuring variations in the optical characteristics and properties of a body of regular geometrical form such as a sheet of glass of nominally uniform thickness. The invention can be used for example to measure the angles of prisms or variations in the refractive index of a thin plate of transparent material having parallel opposite surfaces, for detecting and measuring optical defects which may exist in a sheet of glass, and for measuring its light transmitting properties.

An important object is to provide a method and apparatus which enable the determination and correction of imperfections in sheet glass during its manufacture. A large percentage of sheet glass of high quality is, at the present time, produced by procedures consisting in melting raw batch ingredients in a furnace, followed by vertically drawing upwardly from the surface of the bath of molten glass in the furnace, or by drawing the incipient molten glass sheet horizontally over and floating it upon a bath of molten metal such as tin. The main optical defects usually encountered in sheets so manufactured are elongated in the direction in which the glass was drawn, this is in the direction of the draw whether that be vertical of horizontal, as aforesaid. In general the defects are the result of:

a. Local heterogeneities of composition in the glass and, consequently, variations in its index of refraction from one area to the next;

b. Combing, a defect resulting from localized differences in temperature or viscosity and which form minute striations and like effects;

c. Distortion, a defect similar to combing but of greater intensity, value and importance;

d. Undulations in the surfaces of the glass and which are of yet more importance.

Defects such as those above named effect small magnifications and when straight and narrow may be likened to cylindrical lenses of variable powers. The power, and hence the intensity of each defect, may be expressed as a derivative or function of the deviation of a ray of light traversing the glass in a direction perpendicular to the flaw, that is, the deviation with respect to that observed in an essentially perfect specimen.

In the prior art, various attempts have been made by empirical or semi-empirical procedures to determine defects in sheet glass by observing changes in the index of refraction or the planarity, by observing deviations of rays of light incident on or traversing the specimen. However, the accuracy of such observations is hampered by diffraction effects so that the degree of precision attainable is not sufficient, particularly in the case of small or minute defects or flaws in structure.

In accordance with the present invention, the article to be tested is scanned with light coming from an extended luminous source or object which has passed through an image-forming objective lens in the vicinity of the article and which is on its way to the formation of a real image of that object. The light from the source may have been stopped down by a diaphragm whose opening has a small dimension parallel to the direction of scan, this diaphragm being in the vicinity of the second principal plane of the objective lens. The extended luminous source lies in a plane parallel to the diaphragm and possesses a similar slitlike shape, of dimensions preferably at least twice those of the diaphragm.

The rays thus incident on and traversing, or reflected at the article under test, are incident upon a differential photoelectric cell located in the plane of the image of the luminous object formed by the objective lens. The cell supplies an output signal which varies with the displacements, even minute, of the image which are produced by irregularities in the article under test. In the examination for example of flat glass, the invention is capable of operating with the luminous object and photocell on opposite sides of the glass sheet under test, and with the light passing either essentially normally or obliquely through the sheet. The invention also includes, however, examination of such flat glass with luminous source object and the photocell on the same side of the glass sheet by reflection either at the near surface or at the far surface of the glass, in the latter case with two traverses through the glass, or, alternatively, upoon reflection of the light from a mirror spaced from the test sheet.

Thus, where it is desired to detect flaws or blemishes in a sheet or ribbon of glass being drawn, the optical apparatus may be advantageously oriented so that the longitudinal axes of the luminous source and the slit of the stop are parallel to the direction of the draw. The sweep of the scanning rays will be perpendicular to the direction of the draw and may be effected by movement of the optical apparatus relatively to the sheet, or vice versa. The signal of the photoelectric cell output circuitry can be used directly, or following treatment in one or several ways. In a generally advantageous procedure, the signal is utilized after high and/or low pass filtering, differentiation, rectification and recording.

The method may be carried out by apparatus subsequently described, it being understood that the means shown and described is set forth in a purely illustrative rather than a limiting sense.

BRIEF DESCRIPTION OF THE DRAWING

FIG. 3 is a detail view of the photoelectric cell of FIG. 1 shown rotated through 90°;

FIG. 4 is similar to FIG. 1 but showing a modified form of apparatus in accordance with the invention wherein there are two traverses of the sheet by the scanning beam, with an intermediate reflection by a mirror;

FIG. 4 is a block diagram showing the circuitry by which the signal detected by the cell of FIG. 1 is treated;

DESCRIPTION OF THE PREFERRED EMBODIMENTS

Figures 1, 2:
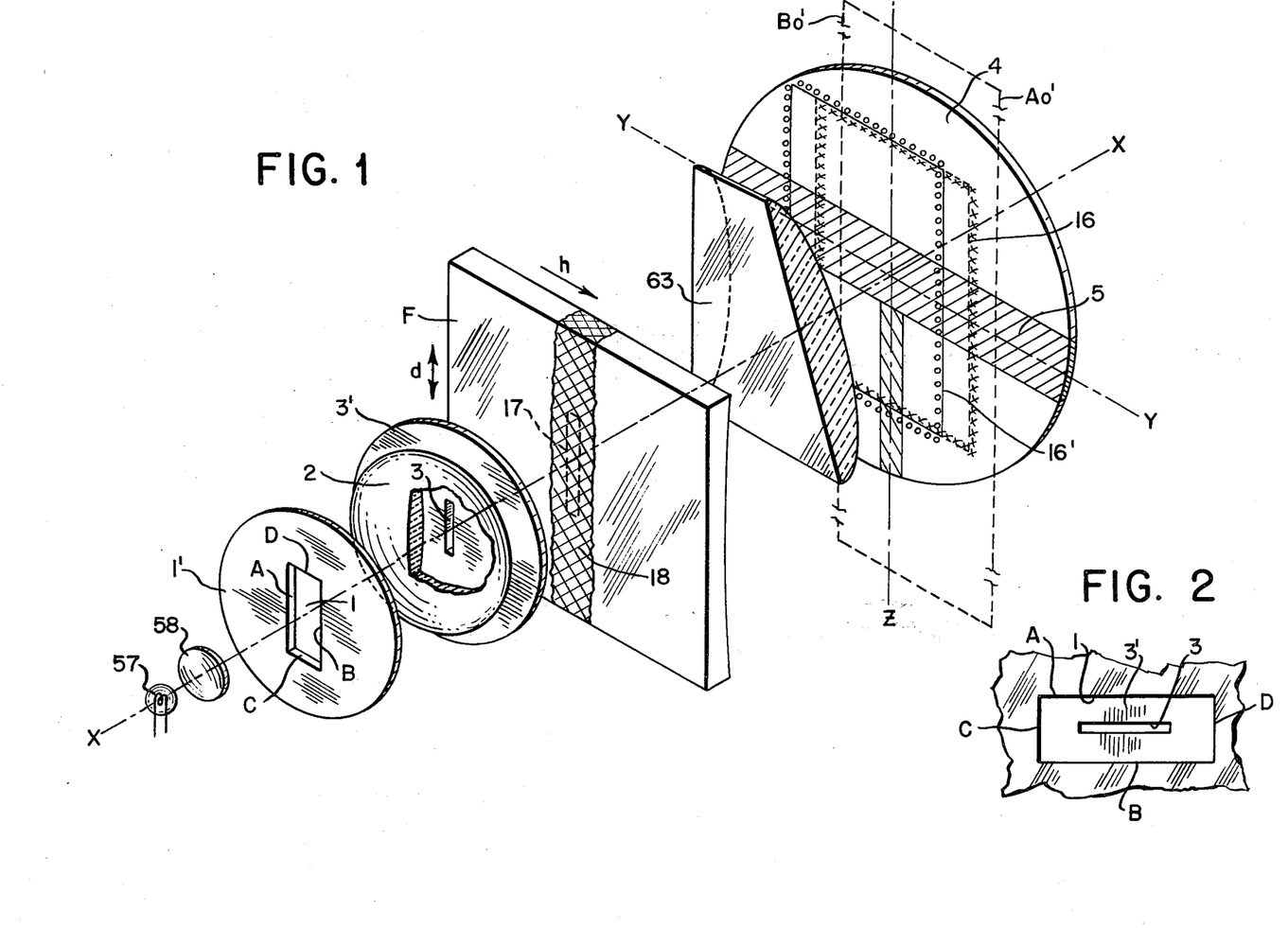
FIG. 1 shows schematically one form of apparatus according to the invention.
FIG. 2 is a fragmentary view of the source — defining means and beam stop in the apparatus of FIG. 1.

Referring to FIG. 1 which for clarity of illustration is not drawn to scale, reference character 1 denotes an opening in a diaphragm 1', the opening being uniformly illuminated from a source such as a lamp 57 with the help of a condenser lens 58. Reference character 1 thus denotes an extended luminous source, which constitutes the object of which an image is produced by the lens 2 to be mentioned presently. The source is desirably of rectangular shape, and may have two long sides A and B and two short sides C and D, these being the sides of the opening in the diaphragm 1'.

To the right of the source is disposed an image-forming means such as a lens, indicated at 2, which forms, from light emerging from the diaphragm 1', a convergent beam containing a real image of the source 1. This beam, after passage through a sheet F undergoing test and through an anamorphic lens 63, comes to a focus in an image plane occupied by a differential photocell 4 and there forms a real image of the source 1. Assuming the sheet F to be, in the region thereof instantaneously explored by the beam, a plane parallel plate without defect, the image will have a shape such as that indicated by the rectangle of crosses identified by reference character 16. The image is reduced in height along the Z—Z axis shown in the figure by the power, in the meridian of that axis, possessed by the lens 63. Of course, the greater power in that meridian, which contains the system axis X—X and the axis Z—Z above referred to, will mean a shorter focus for the system in that meridian than in the perpendicular meridian containing the system axis X—X and the transverse axis Y—Y at the image plane of cell 4. Since however, the instrument is not a visual one, this split in foci is unimportant. Assuming the plate F to have a defect in the portion thereof traversed by the beam, the image will be displaced to a position such as that indicated by the rectangle 16' of small circles.

If the defect, like the defect 18 shown, is a defect such as a striation extending substantially parallel to the axis Z—Z, which is the direction in which the glass has been drawn (identified by the arrow d in FIG. 1), the image shift will be along the axis Y—Y. The photocell 4 and associated equipment signal this shift in the image, which occurs as the sheet F is moved relatively to the other elements in the direction h parallel to the axis Y—Y when the defect 18 reaches the location 17 where the beam carrying the image of source 1 passes through the sheet F.

A second diaphragm or stop 3' having an aperture 3 is desirably located parallel to and adjacent the objective lens 2. The effect of diaphragm 3 is to stop down, at the axial location of the sheet F, to the dimensions of the rectangle 17, the cross-section of the convergent beam formed by lens 2 from light diverging from the extended luminous object 1. As is seen in FIG. 2, the apertures 1 and 3 are in parallel plans, are of rectangular form, and have their longitudinal and transverse dimensions respectively parallel. The width of aperture 1 is several times, at least twice, the width of aperture 3. The width, that is the short dimension, of aperture 3, is chosen so that the width of the area 17 illuminated by the beam incident on the article under test is preferably less than one third the width or half period of an elongated defect, indicated at 18, usually encountered in drawn glass.

Thus the concentrated rays from the extended luminous source, constituted by aperture 1, are focused by objective lens 2 into a convergent beam and then stopped down by aperture 3 so as to illustrate a slit-shaped area 17 on the sheet of glass F being tested parallel to the long dimension of defect 18. After passing through the sheet F, the beam traverses an anamorphic lens 63, to form an enlarged inverted real image, identified at 16, upon a differential photoelectric cell generally indicated at 4 and further shown in FIG. 3. By operation of the anamorphic lens the long sides $A'_o$ and $B'_o$ of the image of source 1 formed by objective lens 2 are compressed to form an approximately equidimensial or nearly square shaped image 16. While the anamorphic lens will produce a split in the foci of the optical system, this does not affect the operation of the invention.

Figures 3, 4, 6:
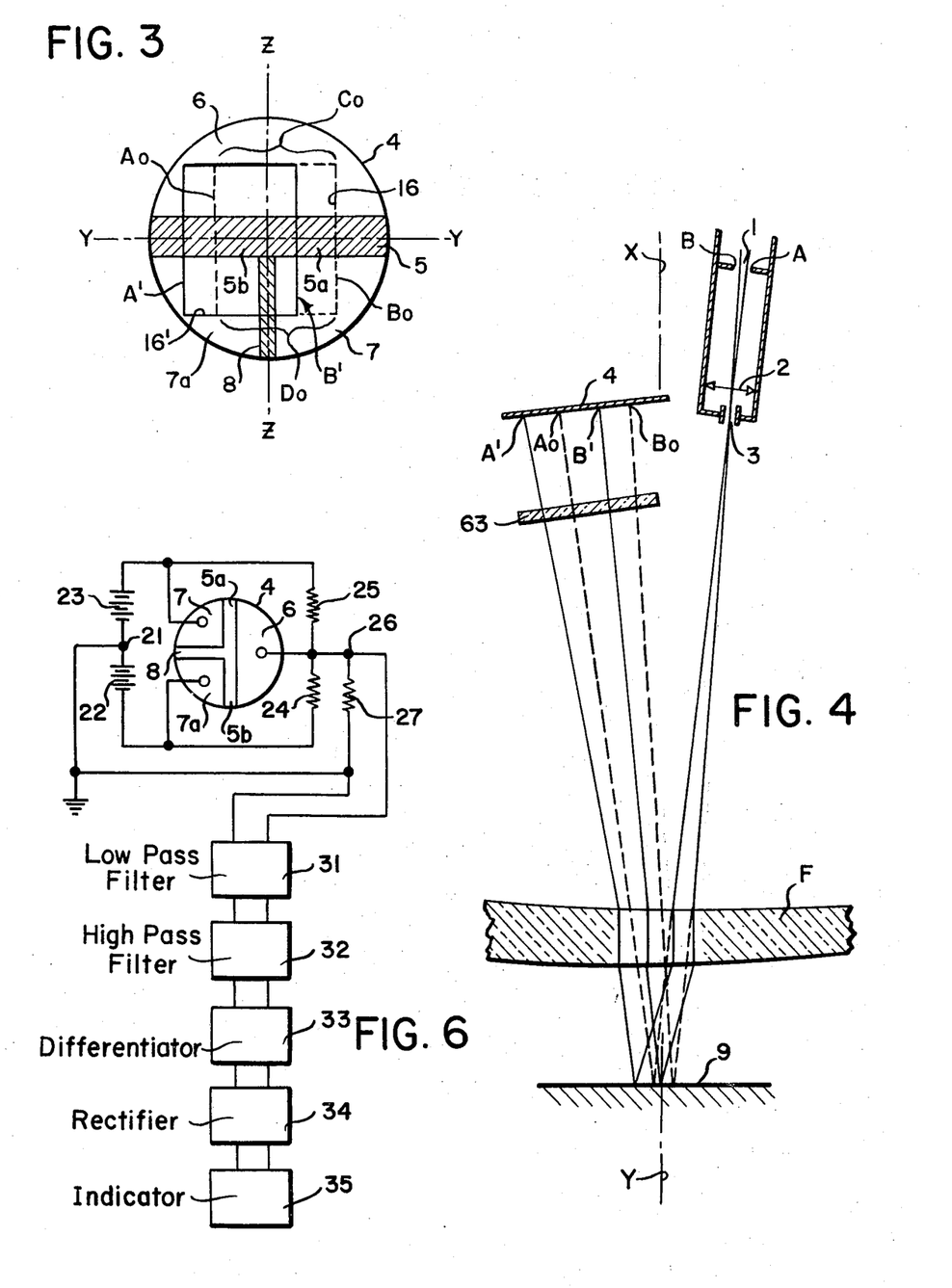

The photoelectric cell 4 is further shown in FIG. 3. It includes a strip 5 of photoconductive material, an electrode 6 contacting the strip 5 along one of the long sides of the striip, and two electrodes 7 and 7a each contacting the strip 5 along substantially one-half of its other long side. The electrodes 7 and 7a are separated from each other by a neutral strip 8 which may be formed either of photoconductive material or of insulating material. The cell 4 is oriented with respect to the source 1 of FIGS. 1 and 2 so that the longitudinal axis Y—Y of the strip 5 in FIG. 3 is parallel to the short sides C and D of that source. Z—Z is an axis perpendicular to axis Y—Y, and like axis Y—Y is in the plane of the image of the surface of the strip 5, and passes through the neutral strip 8. The halves of the strip above and below axis Z—Z may be called 5a and 5b. The dash line rectangle 16 in FIG. 3, corresponding to the rectangle of crosses 16 in FIG. 1, denotes the rectangular image of the source 1 formed on the photocell by the objective lens 2 and anamorphic lense 63 when the test piece F is without flaw in the portion thereof traversed by the light which makes up this image and which is passed by the stop 3'. In the event of a flaw, the image is displaced to a position such as that indicated by the full line rectangle 16', corresponding to the rectangle of small circles 16' of FIG. 1. The cell is desirably so positioned with respect to the source 1 and lens 2 that the undeviated image 16 in FIG. 3 extends equally above and below the axis Z—Z.

Referring to the circuit diagram of FIG. 6, voltage sources 22 and 23 are connected in series between electrodes 7 and 7a with the junction 21 of those sources being grounded. Resistors 25 and 24 are also connected in series between electrodes 7 and 7a with the junction 26 of those resistors being connected to the electrode 6. The voltage difference between points 21 and 26 is applied across an output impedance 27. The impedance 27 feeds a low pass filter 31 described below.

In the absence of a test specimen, or when a specimen, although present, is essentially free from imperfections over the small area thereof traversed by the light rays from the source which are focused by lens 2 and passed by stop 3', the image 16 of slit 1 is centralized with respect to the axes YY and ZZ of light sensitive strip 5, and the output signal of terminals 26 and 21 is of a reference value.

However, when a sheet F is in position as in FIG. 1 and has at the area 17 traversed by the light rays a defect such as for instance, a lack of true planarity or abnormal index of refraction, the image 16 is shifted, as shown exaggeratedly in FIG. 1, to a location 16' in the plane of the face of cell 4.

As indicated in FIG. 3, when the image 16 shifts, as a result of defect in sheet F, to a location 16', the illuminated area of half-strip 5a is decreased while the illuminated area of half-strip 5b is increased. The change in the areas illuminated by the shift of the image results in a voltage between points 26 and 21, of the circuit shown in FIG. 6, which is difficult from the reference voltage present at these terminals when the image is at the location 16. The difference between the reference voltage produced by the shifted image is a function of the shift in the image and hence of the magnitude of the optical defect in the body being tested. The differential voltage thus resulting may be treated in a number of ways. FIG. 6 shows one such way wherein a low pass filter 31 and a high pass filter 32, or an equivalent band pass filter, and a differentiator 33, a rectifier 34, and a register, recorder or indicator 35 are serially connected in the order mentioned. The invention also makes possible direct utilization of the output signal from the terminals of resistance 27, to afford a graph of deviations. When the signal is integrated, a graph can be prepared giving variations in thickness of the sheet or ribbon of glass.

The parameters of the optical system are chosen so that the width, $C_o$ or $D_o$, in FIG. 3, of the image 16 is less than longitudinal dimension of strip 5, and the shifted image is at all times completely incident upon the strip 5 up to the maximum magnitude of the defect which the instrument is capable of detecting or sensing.

Preferably the intensity of illumination of image 16 is sufficiently great so that the illuminated portions of the areas 5a and 5b operate at saturation. This has the double advantage that the sensitivity of the instrument is at a maximum, while at the same time, variations in output signals otherwise caused by accidental and undesired variations in the intensity of incident light, are avoided. Thus the instrument is made solely responsive to the difference in the illumination of the areas 5a and 5b.

To obtain the desired sweep of the specimen, for instance a sheet of drawn glass, the apparatus is oriented so that the longitudinal axes of slits 1 and 3 and the axis Z—Z of cell 4 are parallel to the direction of the draw, indicated by arrow d in FIG. 1. The apparatus is then displaced or translated transversely of the sheet in a direction perpendicular to the direction of the draw as indicated by arrow h, FIG. 1. Hence, the beam scans the sheet under test transversely of the long dimension of a typical defect encountered in drawn glass. Flaws in the sheet will deflect the beam resulting in an instantaneous shift of the image and creating a like instantaneous variation in the output signal of the cell. Scanning may thus be effected successively along a multiplicity of closely-spaced parallel linear paths to encompass the entire area of the sheet or ribbon.

The apparatus thus described can be used to scan and test for defects distributed over the entire area of a sheet of glass drawn or being drawn. Alternatively, of course, the instrument may be used to scan any particular local area of a sheet. Thus the output signal from cells 4 affords reliable indications of the value or importance of any defects or defective areas in the glass, and can be made to supply numerical values which agree satisfactorily with those obtained by prior art empirical procedures.

If the angle of incidence of the scanning beam is oblique, that is, if its angle of incidence on the sheet is adjusted to make an angle of up to 30° with respect to the normal to the sheet at that point, and the sheet has been found to be essentially free of minor defects and imperfections, the increased sensitivity enables a very satisfactory detection of accidental and undesired undulations, by filtering out higher frequencies of the output signal.

Under the condition wherein the scanning beam is normal to the area being instantaneously scanned, and provided that the aperture 3 is sufficiently small, the invention also makes possible study of variations in the index of refraction of a transparent object, by use of a thin lamination having parallel faces, immersed in a body of liquid having a similar index of refraction.

Figures 5, 9:
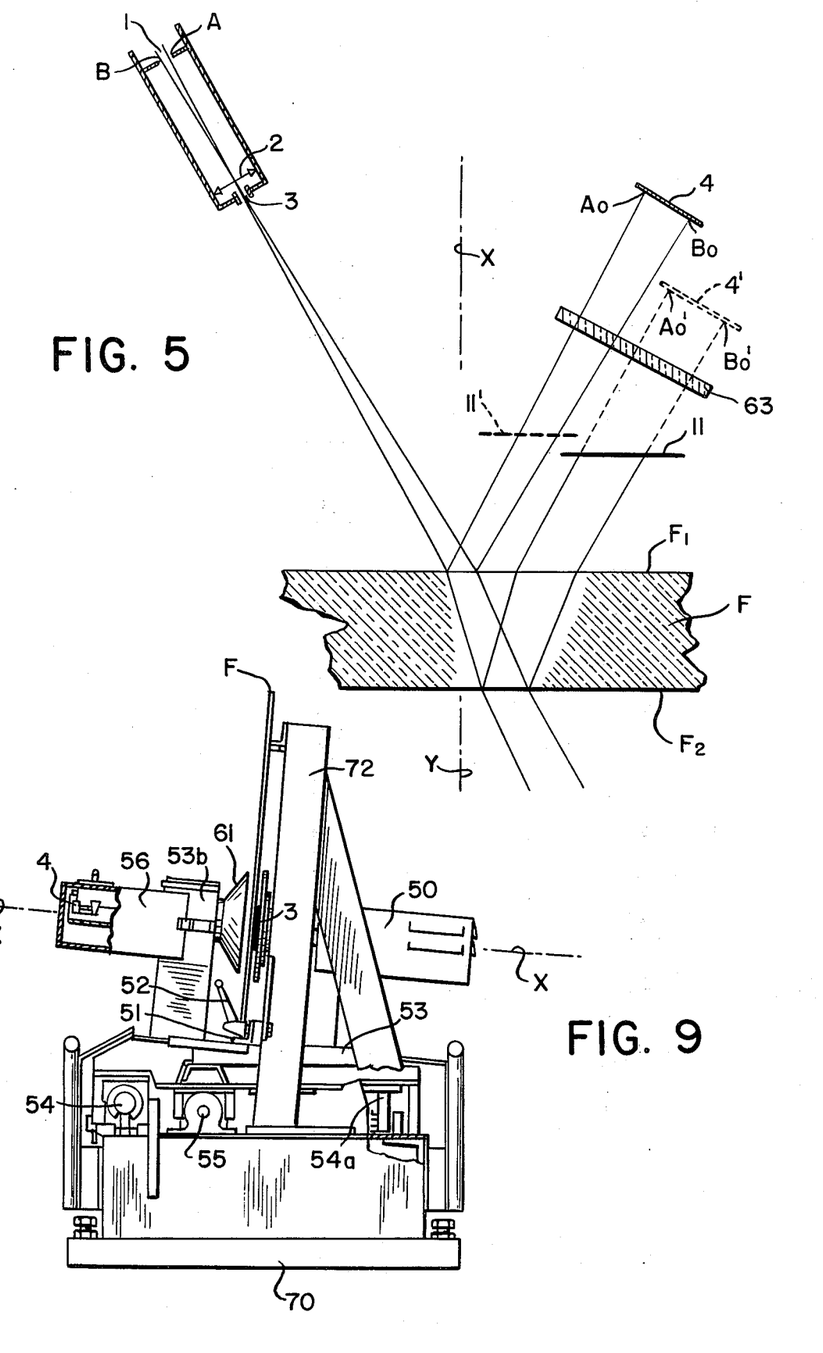
FIG. 5 shows another form of apparatus in accordance with the invention, also similar to FIG. 1, but in which there occurs one reflection from the upper or adjacent surface of the glass or, alternatively, a reflection of the beam from the lower or remote surface of the sheet with an intermediate two traverses or the sheet.
FIGS. 7, 8 and 9 are views in plan, front elevation and side elevation respectively, showing means for mounting an apparatus according to the invention and capable of use in scanning and testing, over its entire area, a sheet of glass supported on those means.

Essentially the same principle is involved in the apparatus schematically shown in FIG. 4, wherein the same reference characters are used to identify the parts corresponding to those in FIG. 1. For simplicity of the drawing, FIGS. 4 and 5 show only two of the rays which make up the scanning beam, namely rays from the side edges A and B (FIG. 1) of the object 1 which pass through the center or nodal point of lens 2. Referring to FIG. 4, the rays emerging through slit 3 pass through the test specimen or glass sheet F, and are then incident upon a reflector such as mirror 9. The reflected rays again traverse the specimen, than the anamorphic lens 63, and, if the portion of the sheet illuminated thereby is without defect, are incident upon cell 4 at points $A_o$ and $B_o$ as previously described. With a defect present, the rays are shifted to points A' and B'. To position the source and cell on the same side of the specimen F, it is necessary to incline the rays at an appreciable angle to the central axis X–Y, FIG. 4, normal to the sheet or specimen and either parallel or perpendicular to the direction of analysis determined by the width of the aperture, that is to say, the direction of width C or D of objective aperture 1 and that of slit 3, and by the longitudinal axis Y—Y of sensitive areas 5a and 5b of the cell. In general the direction of analysis aforesaid may be in the plane of the figure as in FIG. 4, or perpendicular to that plane, depending upon the nature of the principal defects it is desired to identify. The sheet F may be displaced or translated relatively to the described apparatus, in a direction normal to the axis X–Y, FIG. 4, either in the plane of the figure or transversely to that plane. Except for mirror 9, which is firmly fixed with respect to the apertures 1 and 3, to the objective 2, to the anamorphic lens 63 and to the photocell 4 so as to be free of angular vibrations or play, all parts of the instrument are positioned upon the same side of the sheet. The arrangement of FIG. 4 is of particular advantage in industrial applications such as scanning and testing a continuously moving ribbon of glass, as by mounting the apparatus on a bridge enabling it to be translated back and forth parallel with the ribbon and normal to its translation in the direction of its length.

Referring to FIG. 5 wherein two modes of operation are shown, the projected rays make an appreciable angle with respect to the principal axis X–Y. As shown, the angle is preferably about 30°. Assuming sheet F to be essentially free of defects, the incident rays are reflected at an equal angle from the near face $F_1$, and impinge on a cell 4 shown in full lines. In that particular use, indicated in solid lines, rays reflected from the lower face $F_2$ of the sheet are eliminated by a screen 11. Those spurious rays may also be eliminated by immersion of surface $F_2$ in a liquid having the same index of refraction as the glass. In the particular manner of use being described, defects in upper surface $F_1$ are detected separately and apart from internal defects such for example as variations in the index of refraction and defects in the remote surface $F_2$. Such a separation is desirable and useful, in particular in laboratory investigations. It is of interest to note that the direction or plane of analysis may be perpendicular to the plane of FIG. 5 to thus increase the significance of the physical output readings, provided that the height of the diaphragm as thus located, is not excessive and thus enables the essential separation as aforesaid.

In the second mode of operation of the invention depicted in FIG. 5, with a cell 4' at the position indicated in dashed lines, the screen 11 is eliminated and is replaced with a screen 11'. The cell 4' therefore receives the scanning beam after two traverses of sheet F and an intermediate reflection from the lower surface $F_2$ of the sheet. In this mode of operation the lengths A and B of aperture 1 as well as that of aperture 3 and axis Z—Z of the cell, may advantageously be perpendicular to the plane of the figure. Thus the kind of measurement is the same as visual observation if the sheet should be used for making a silvered mirror with a silvered face on lower surface $F_2$. The displacement of the scanning rays will be perpendicular to the axis X–Y, for instance, in the plane of FIG. 5, or perpendicular to such plane.

As an example the following physical values relate to an instrument giving very satisfactory results:

Waviness and combing are measured about axes perpendicular to the general direction of the defects, by adjusting low pass filter 31, FIG. 6, to eliminate frequencies above 16 Hz (thus also suppressing basic noise and random peaks), and by adjusting high pass filter 32 to a frequency which may be between about 1 and 4 Hz. The pitch of the defects is to a certain degree related to the half-period of a sinusoidal wave. Distortion is measured by adjusting low pass filter 31 at 1 to 4 Hz.

When one is to measure undulations, the power of which is small and the half-wave length of which is about 100mm, it may be necessary to employ an oblique angle of incidence of about 30° to the vertical and an increase in the scanning velocity to about 10 cm/sec. The low pass filter will then be adjusted to about 1 Hz.

As will be clear from the very small dimensions above given, it is not possible to study and explain the operation of my invention on the basis of pure geometrical analysis or values. Thus, while up to the present I have not been able to advance a positive theoretical explanation of the principles of operation underlying the invention, I have by actual use, obtained satisfactory results in the location and measurement of imperfections in a specimen or sheet of glass.

Figure 7:
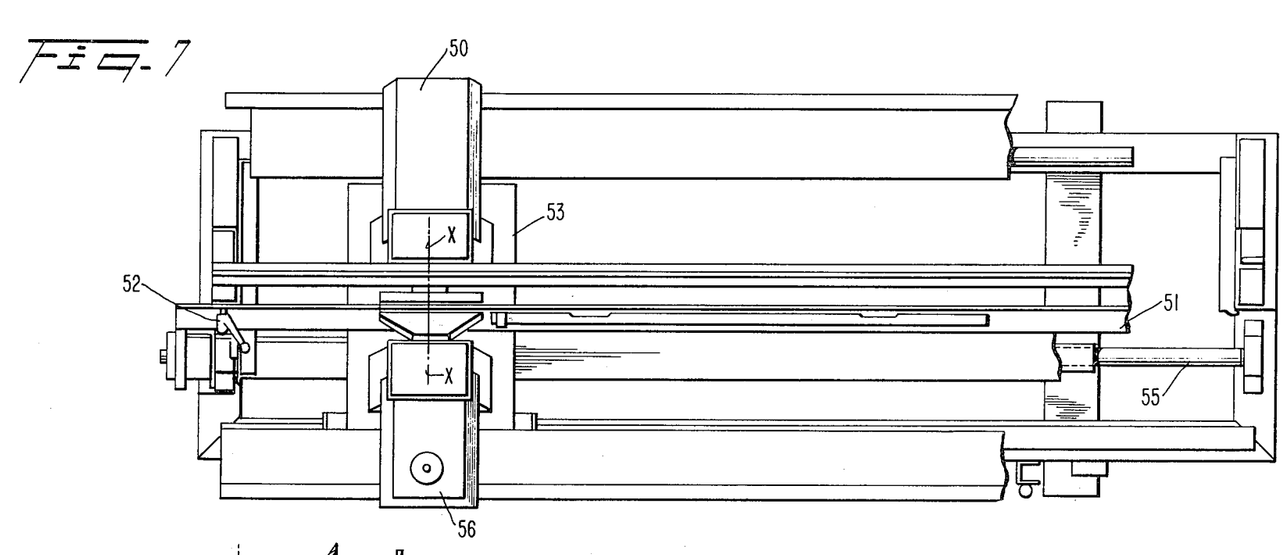
Figure 8:
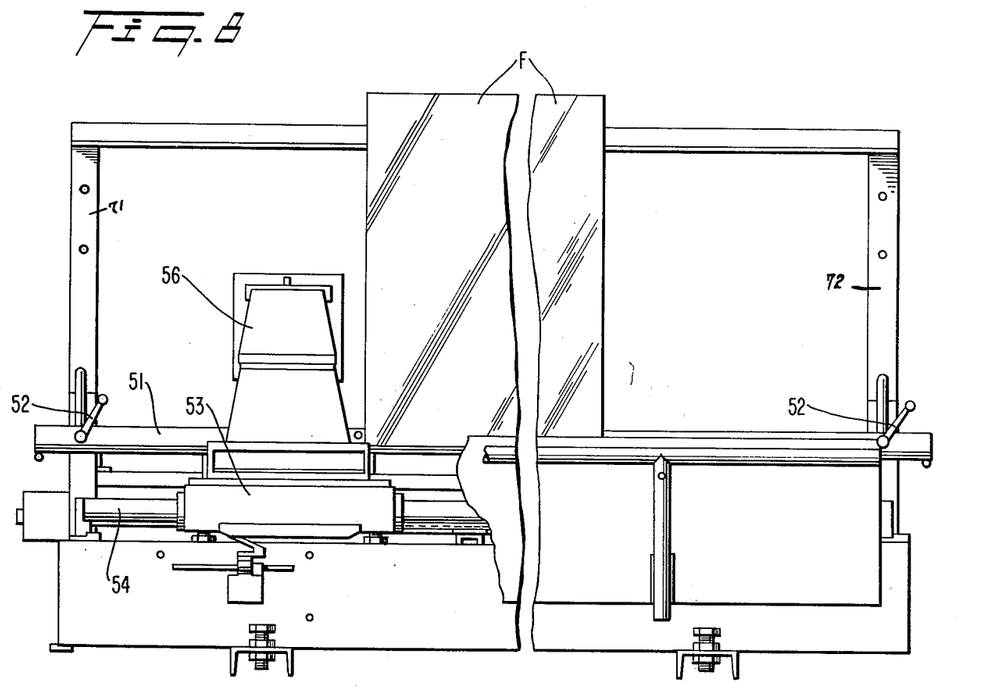

Referring to FIGS. 7, 8 and 9, there is shown in plan, front, and side elevations, respectively, an apparatus by which the optical system of the invention can be controllably moved over a sheet of glass or like transparent material mounted thereon, in order to scan its surface for defects.

A rigid base 70 supports parallel uprights 71, 72 which, as shown upon FIG. 8, support at its ends a rigid straight bar 51. The bar can be fixed in a selected one of a large number of positions of vertical adjustment on and along the uprights, by locking means 52 which may also engage the sheet F at its corners to support the same and to prevent horizontal shifting thereof in its own plane. As seen in FIG. 9 the sheet is supported by the bar at and along its lower edge, and at a slight angle to the vertical.

Base 70 supports a carriage 53 for sliding horizontal translation in a direction normal to the plane of FIG. 9.

| | |
|---|---|
| Width of objective aperture 1 (dimension C or D in FIG. 2) | 1.5 mm |
| Length of objective aperture (dimension A or B in FIG. 2) | 7 mm |
| Distance of objective aperture from objective lens 2 | about 10 cm |
| Focal length of lens 2 | about 8 cm |
| Width of slit 3 | 0.5 mm |
| Length of slit 3 | 3 mm |
| Image distance of objective aperture 1 from objective 2 | about 30 cm |
| Width of image | 4.5 mm |
| Length of image | 21 mm |
| Reduction of length by anamorphorscope to | about 4 mm |
| Angular deviations of the image by scanned defects in the glass between about $10^{-2}$ and $10^{-5}$ radians | |
| Maximum linear deviation of image perpendicular to axis Z—Z, FIG. 3 | about 0.03 mm |
| Diameter of light-admitting opening in cell 4 | about 6.5 mm |
| Distance of separation between electrodes 7, 7a may vary between | 0.2 and 0.5 mm |
| Distance of separation between measuring electrode 6 and electrodes 7, 7a (width of strip 5.) | about 1.0 mm |

Speed of sweep of scanning may vary between about 20 cm/min and 6 m/min, the most-used speed being about 1.5 m/min=2.5 cm/sec.

Translation is effected by a motor, not shown, coupled through suitable gearing to a drive screw 55 and which releasably engages a nut fixed with the carriage. The carriage includes two columns 53a and 53b, fixed with respect to each other, which rise on opposite sides of the position of the piece under test, as indicated in FIGS. 10 and 11.

Carriage 53 mounts the optical scanning apparatus previously described, its principal axis being indicated at X—X, FIGS. 7 and 9, and which is as shown, normal to the plane of sheet F. AT 50, is identified the illuminating means shown in greater detail and to an enlarged scale upon FIG. 10, and mounted at the right side of the sheet as the parts are viewed upon FIG. 9. At the other side of the sheet is firmly supported the photoelectric cell assembly, shown in greater detail and to an enlarged scale upon FIG. 11. It will be understood therefore that the parts located at the right and left sides of the sheet as in FIG. 9, are rigidly interconnected and moved by the screw 55 as a unit, in horizontal translation.

Thus the sheet may be scanned for defects over its area, by translating the carriage 53 back and forth along tracks 54, 54a, with a small change in elevation of bar 51 between passes of the carriage. Alternatively, of course, any selected area only of the sheet may be scanned and investigated.

Figure 10:
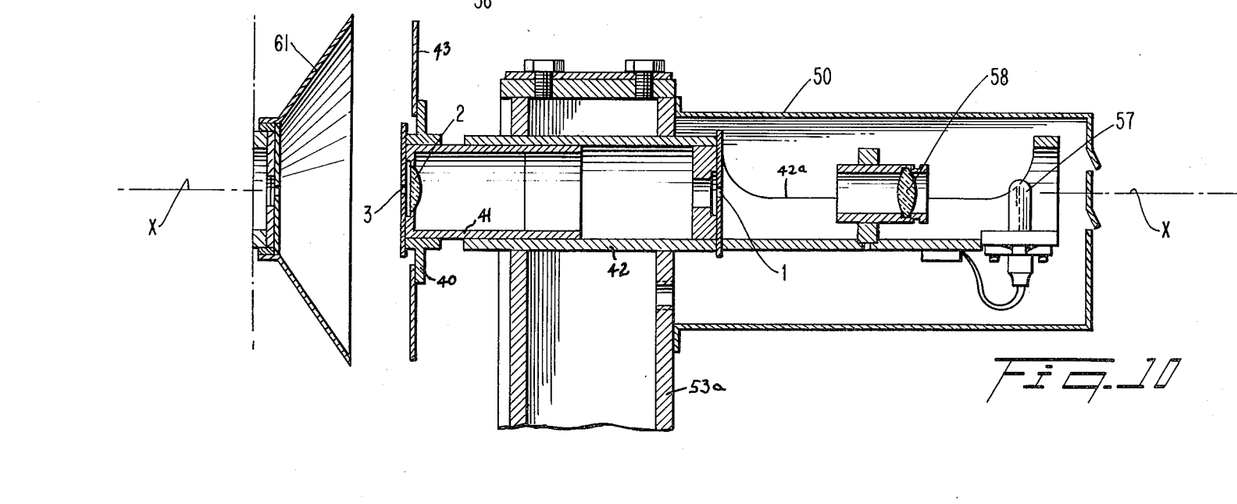
FIG. 10 is a vertical sectional view to an enlarged scale, through the central or principal optical axis thereof, of that portion of the apparatus of FIG. 9 disposed, as seen in FIG. 9, at the right of the sheet to be scanned.
Figure 11:
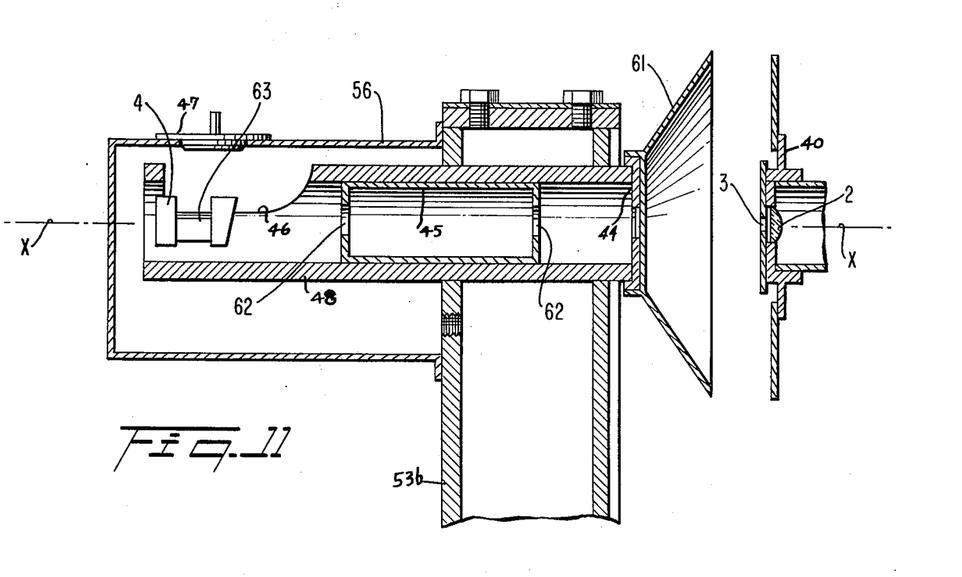
FIG. 11 is a vertical sectional view corresponding to FIG. 10 but showing that portion of the optical apparatus disposed at the left of the sheet, as viewed in FIG. 9.

Turning to FIG. 10, a column 53a is shown, supporting a tube 42 coaxially of axis X—X, and mounting the diaphragm having aperture 1 therein, as previously described in connection with FIG. 1. Objective 2 and its diaphragm with aperture 3 are shown as mounted in a cover 40 over one end of a tube 41 adjustable axially for a limited distance in and along a main tube 42 of larger diameter. Rearwardly of apertured diaphragm 1, a source of illumination is shown as a filament lamp 57 mounted in one end of tube 42. A condensing lens 58 is also mounted in tube 42, as at 58, so that a beam of rays from source 57 is projected to and through aperture 1. All optical parts such as apertured diaphragms 1 and 3, and lenses 2 and 58 may be mounted for limited adjustment in and along axis X—X, in order to calibrate the instrument. Tube 42 itself may be mounted for a corresponding limited axial adjustment. As shown upon FIG. 10, tube 42 is cut away as at 42a at its right end, to afford access to condenser 58 and to afford circulation of cooling air. A protective cap 50 having louvered apertures for circulation of cooling air, is fixed to carriage part 53a to enclose the right end of tube 42 and the parts mounted therein. A circular shield 43 has a central aperture forming an inner rim secured to the circular flange formed on cover 40.

At the left side of sheet F, as viewed in FIG. 9, and referring in particular to FIG. 11, wherein apertured diaphragm 3 and objective lens 2 are also shown, a member 53b of carriage 53 supports a horizontal tube 48 with central axis coincident with axis X—X. The right end of the tube is covered by a centrally apertured cap 44 equipped with a hood 61 and which in cooperation with shield 43 screens out parasitic rays, fits over the tube and is also centrally apertured.

A short tube 45 having closed ends centrally apertured as at 62, fits within tube 48 for limited axial adjustment therealong. At the left end of tube 48 which is there partially cut away as indicated at 46, is mounted the photoelectric cell 4 previously described, with anamorphoscope 63 interposed between it and apertured tube 45. A protective cap 56 having removable access cover 47 encloses the portion of tube 48 protruding to the left, FIG. 11, and parts mounted therein.

OPERATION

Operation of the instrument and apparatus has been in the main, previously set forth and explained, but may be briefly resumed as follows:

A sheet F to be scanned or tested for defects affecting its optical characteristics, is mounted with its lower edge on and supported by bar 51, adjusted vertically with respect to uprights 71, 72 so that the area or linear element to be investigated, is at the level of axis X—X. With lamp 57 and the circuitry of FIG. 6 energized, and the carriage 53 positioned at one end of tracks 54, 54a, the motor driving feed screw 55 is energized and the carriage and optical test instrument mounted thereon, move horizontally across the sheet, toward the other end of the tracks. When the minute area of sheet F being thus instantaneously scanned and traversed by the scanning beam is essentially free from defects, the output signal from cell 4 is at its calibrated reference value. When the area instantaneously traversed is imperfect by reason for example, of combing, wedge or lack of parallelism between surfaces, increased or decreased thickness of the area, from normal, etc., the scanning beam is thereby deflected in one or the opposite direction, to impinge a greater area of sensitive strip 5b for instance, and a correspondingly smaller area of strip 5a.

The balance between voltages applied at terminal 21, FIG. 6, is thereby upset. The current between electrode 7a and measuring electrode 6 is increased, while that between electrodes 6 and 7 is decreased. The differential voltage applied between terminals 21 and 26 creates an output signal which in the way previously described, is treated and measured as a function of the optical importance of the defect. Tubes 42 and 48 may be rotated through the same angle, 90° for example, about axis X—X, and with respect to supports 53a, 53b, when it is desired to investigate defects such as striations or combing extending in the plane of the sheet, normal to, or at other known angle to, the direction of translation of carriage 53 over and with respect to the sheet or specimen.

It will thus be seen that the invention provides apparatus for testing a body for optical defects, such apparatus comprising an extended luminous source such as the diaphragm aperture 1 of FIG. 1, a differential photocell such as the cell 4, focusing means such as objective lens 2 to form from light diverging from that source a convergent beam carrying an image of the source which comes to focus at the location of the photocell, and means connected to the photocell for producing an output signal upon displacement of the image on that element. Advantageously the apparatus further includes means, such as the diaphragm 3, to limit in at least one direction the transverse dimension of the beam at the location of the interposed object being tested to a dimension of the same order of magnitude as the transverse dimension of typical defects being investigated.

Similarly, it will be seen that the invention provides a method of testing a body for optical defects comprising focusing light rays from an extended luminous source as the source 1 in FIG. 1 toward an image location in the plane of a photoelectric cell, stopping down the focused rays in at least one direction transverse of the direction of propagation thereof, interposing the body in the path of the focused rays at a position between the source of the image location to illuminate the body over an area limited in at least one direction by a dimension of the same order of magnitude as the short dimension of a typical defect, effecting relative advance of the body on the one hand and the source focusing means stop and cell on the other hand with a motion including a component parallel to that direction and detecting shifts of the image of the source at said image location.

While the invention has been described hereinabove in terms of a number of presently preferred embodiments of the apparatus thereof, and in lieu of the presently preferred practice of the method thereof, the invention is not limited thereto, but rather comprises all modifications of and departures from those embodiments and from that practice properly falling within the scope of the appended claims.

I claim:

1. Apparatus for testing a body for optical defects, said apparatus comprising:
   a. an extended luminous source,
   b. focusing means for forming, from light from said source, an image of said source at an image location,
   c. means to support said body in the path of the beam at a position between said focusing means and sasd image location,
   d. a photoelectric cell disposed substantially at said image location, said cell having an extended light-sensitive element and being responsive to the positional shift of said image on said element, and
   e. circuit means connected with said cell for producing an output signal upon displacement of said image on said element.

2. Apparatus according to claim 1 further including indicator means responsive to said output signal, said indicator means being electrically connected to said circuit means.

3. Apparatus according to claim 1 wherein said image-forming means includes at least one focusing element, to form said image of said extended luminous source and at least one anamorphic element positioned between said position where the body is supported and said cell to render said image substantially equidimensional.

4. Apparatus according to claim 1 including a stop having an extended aperture to stop down said beam so that the area illuminated by said beam on said body is in at least one direction of a dimension of the same order of magnitude as the short dimension of said defect.

5. Apparatus according to claim 1 in which said apparatus includes means for supporting said source, image-forming means and cell on said apparatus, in position so that rays from said source are received from said body on said element, and means for moving one of said support means relative to the other to scan said body.

6. Apparatus according to claim 1 in which said apparatus includes means for supporting said source, image-forming means and cell on one side of said body.

7. Apparatus according to claim 6 further including reflecting means, said means for supporting said source, image-forming means and cell mounting said reflecting means in fixed relation with said luminous source, with said focusing means and with said cell so that said rays are received from said body by said reflecting means and are diverted by said reflecting means to said element, said reflecting means being supported on the other side of said body.

8. Apparatus according to claim 1 wherein said photoelectric cell includes at least one electrode disposed on one side of said element and in electrical contact therewith and a plurality of electrodes disposed on the other side of said element and in electrical contact therewith.

9. Apparatus according to claim 8 further including an insulating strip for insulating said electrodes of said plurality of electrodes from each other.

10. A method of testing a body for optical defects comprising the steps of focusing light rays from an extended luminous source toward an image location, interposing said body in the path of said focused rays at a position between said source and said image location to illuminate said object over an area limited in at least one direction by a dimension of the same order of magnitude as the short dimension of a typical defect, advancing said body with a motion including a component parallel to said direction, and detecting shifts of the image of said source at said image location.

11. A method according to claim 10 wherein said focused rays are stopped in said direction to a dimension of the same order of magnitude as the short dimension of a typical defect in said body.

12. Apparatus for testing a body for optical defects, said apparatus comprising an extended luminous source, focusing means to form an image of said source at an image location, means to support said body in the path of a beam formed by said focusing means from light from said source at a position between said focusing means and said image location, a stop having an extended aperture and disposed in the path of said beam at a position between said focusing means and said position where the body is supported to stop down said beam so that the short dimension of the area illuminated by said beam on said body is of the same order of magnitude as the short dimension of a typical defect, a photoelectric cell disposed substantially at said image location, said cell having an extended light-sensitive element and being responsive to the positional shift of said image, an anamorphic element disposed in the path of said beam between said position where said body is supported and said cell to reduce the dimension of said image in a direction transverse to the long dimension of said element, said apparatus including circuit means connected with said cell for producing an output signal upon displacement of said image on said element.

13. Apparatus according to claim 12 wherein said image has an intensity of illumination sufficiently great to saturate the illuminated area of said element.

* * * * *

UNITED STATES PATENT AND TRADEMARK OFFICE
CERTIFICATE OF CORRECTION

PATENT NO. : 3,989,387
DATED : November 2, 1976
INVENTOR(S) : Stephane HATEGAN

It is certified that error appears in the above-identified patent and that said Letters Patent are hereby corrected as shown below:

Column 2, line 24, for "upoon" read -- upon --.

Column 2, line 63, for "FIG. 4" read -- FIG. 6 -- .

" ", line 14, for "illustrate" read -- illuminate --

" ", line 31, for "striip" read -- strip -- .

Column 6, line 6, for "cells 4" read -- cell 4 -- .

" ", line 39, for "than" read -- then -- .

Column 10, line 68, for "of" read -- and -- .

Column 11, line 26 (claim 1(c)), for "sasd" read -- said --.

Signed and Sealed this

Fifth Day of April 1977

[SEAL]

Attest:

RUTH C. MASON
Attesting Officer

C. MARSHALL DANN
Commissioner of Patents and Trademarks